United States Patent [19]
Ryan et al.

[11] Patent Number: 4,514,336
[45] Date of Patent: Apr. 30, 1985

[54] HOMOLOGOUS CARBOXYLIC ACIDS PRODUCTION

[75] Inventors: Robert C. Ryan, Houston; Lynn H. Slaugh, Cypress, both of Tex.

[73] Assignee: Shell Oil Company, Houston, Tex.

[21] Appl. No.: 382,988

[22] Filed: May 28, 1982

[51] Int. Cl.$^3$ .................... C07C 51/12; C07C 53/08; C07C 53/122; C07C 53/124
[52] U.S. Cl. .................................. 260/413; 518/716; 560/232; 562/497; 562/517; 562/519; 568/671; 568/698; 568/902; 585/733
[58] Field of Search ............... 562/517, 519, 497; 260/413, 410.9 R; 560/232, 114

[56] References Cited

U.S. PATENT DOCUMENTS

| 2,135,451 | 11/1938 | Loder | 562/519 |
| 3,717,670 | 2/1973 | Schultz | 562/519 |
| 3,769,329 | 10/1973 | Paulik et al. | 562/519 |
| 4,260,820 | 4/1981 | Knifton | 562/517 |
| 4,334,092 | 6/1982 | Knifton | 562/517 |

FOREIGN PATENT DOCUMENTS 47-3332  1/1972  Japan .................... 562/519

Primary Examiner—Vivian Garner
Attorney, Agent, or Firm—Ronald L. Clendenen; Ronald R. Reper

[57] ABSTRACT

A process for homologating alcohols and/or acids to a mixture of higher acids by reaction with syngas in the presence of a ruthenium-rhodium-iodide-titanium(IV) catalyst.

2 Claims, No Drawings

HOMOLOGOUS CARBOXYLIC ACIDS PRODUCTION

FIELD OF THE INVENTION

This invention relates to a process for converting alcohols and carboxylic acids to homologous carboxylic acids by reacting alcohols and carboxylic acids with carbon monoxide and hydrogen in the presence of a catalyst comprising ruthenium, rhodium, an iodide promoter and a titanium(IV) promoter.

BACKGROUND OF THE INVENTION

A wide variety of aliphatic carboxylic acids of differing carbon numbers and structures are presently important articles of commerce. These carboxylic acids can be utilized as the acids per se or converted into other useful materials. For example, detergent range carboxylic acids can be converted via hydrogenation into detergent range alcohols which find applications in the detergents products industries. The lower alcohols such as, for example, methanol and ethanol are readily produced from syngas. The lower carboxylic acids such as, for example, acetic acid and propionic acid can readily be prepared from methanol and ethanol, respectively, by carbonylation. A process that would convert these lower alcohols/acids to higher numbered carboxylic acids would be extremely useful. Knifton in U.S. Pat. No. 4,260,820, issued Apr. 17, 1981, discloses a ruthenium/I catalyst for converting acetic acid to the higher homologs. The catalyst, however, is not particularly effective when dealing with higher molecular weight acids. Paulik et al., U.S. Pat. No. 3,769,329, issued Oct. 30, 1973, discloses a rhodium-iodide system which converts an alcohol to the next higher acid. It does not appear useful for converting an alcohol or an acid to a series of acids.

SUMMARY OF THE INVENTION

This invention relates to a process for converting aliphatic carboxylic acids or aliphatic alcohols to a series of homologous aliphatic carboxylic acids having one or more carbon numbers than the reactant acids or alcohols. The process comprises contacting the reactant acids or alcohols with hydrogen and carbon monoxide in the presence of a homogeneous catalyst comprising a catalytically effective amount of ruthenium and rhodium, an iodide promoter and a titanium(IV) promoter. The catalyst used in the instant invention not only homologates acids to higher carbon numbered acids, but also converts alcohols into the higher numbered acids. The rhodium/ruthenium/iodide/titanium(IV) system continues to homologate acids after the addition of one methylene group to the starting alkanol or starting carboxylic acid. The catalyst used in the instant invention is advantageously used to convert a wide range of alcohols and acids to longer-chained acids, and is not limited to converting lower molecular weight alcohols and acids. The continuous homologation activity of the instant catalyst allows it to be utilized in a continuous process wherein lower molecular weight acids can be recycled to the homologation reactor to be built up into desired long-chained acids. The use of the Rh/Ru/I/-Ti(IV) catalyst enhances the conversion of alcohols and/or acids to acids as compared to the use of the Rh/Ru/I catalyst.

DESCRIPTION OF THE PREFERRED EMBODIMENTS

This process relates to a method for homologating lower molecular weight carboxylic acids and alcohols to a series of higher carboxylic acids. The homologation reactions involved in the instant process are illustrated in Equations 1 and 2 below.

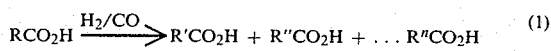

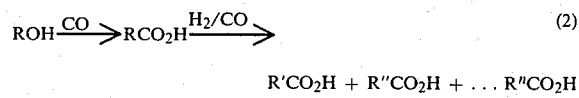

$$R'CO_2H + R''CO_2H + \ldots R^nCO_2H$$

Strictly speaking, homologation refers to the conversion of a compound into one or more of its higher homologs as expressed in Equation 1 above. However, since alcohols in the instant process are converted to an acid having one more carbon atom than the reactant alcohol, and which acid is subsequently converted to even higher numbered acids, homologation, as used in this specification, refers to the conversion of acids and alcohols to a series of higher carbon numbered acids as illustrated by Equations 1 and 2. In the above equations R is a linear, branched-chained or cyclic saturated hydrocarbyl radical containing 1 to about 20 carbon atoms, R' is a similar radical but having one more carbon atom (in a methylene group) than R, R'' is a similar radical having one more carbon atom (in a methylene group) than R', etc. Thus, the homologation reaction of the instant process will produce a homologous series of carboxylic acids with carbon numbers differing by one unit from the nearest homologous member of the series. The number of homologous acids in the series will vary depending on operating conditions and will range from 2 up to a very large number, say 20.

In the broadest aspect of this invention, aliphatic carboxylic acids are prepared from carboxylic acid or alcohol reactants by contacting said reactants with carbon monoxide and hydrogen in the presence of a homogeneous catalyst comprising a ruthenium component, a rhodium component, an iodine-containing promoter and a titanium(IV) compound promoter, and heating said reaction mixture under superatmospheric pressures ranging from about 2,000 to about 10,000 psi until the desired acid products are formed.

In the narrower practice of this invention, aliphatic carboxylic acids having carbon numbers ranging up to about 20 are prepared from aliphatic carboxylic acid or aliphatic alcohol reactants by a process comprising the following steps: (a) contacting said aliphatic alcohol or acid with at least a catalytically effective quantity of ruthenium and rhodium in the presence of an iodine-containing promoter and a titanium(IV) compound promoter with carbon monoxide and hydrogen at a temperature ranging from about 150° C. to about 250° C., and at pressures ranging from about 2,000 to about 10,000 psi until substantial formation of the desired acids has been achieved, and (b) separating said acids from the reaction mixture.

The precise nature and composition of the catalysts used in the instant invention are not known; however, one can specify the catalyst precursors needed to prepare the catalysts. It is postulated that the catalyst is a very complex mixture of rhodium, ruthenium, iodine, titanium(IV) and carbonyl ligands formed into coordination compounds and/or adducts which effect or facilitate catalysis of the instant reaction.

A wide range of ruthenium catalyst components may be utilized to prepare the catalysts of the instant invention. The ruthenium may be introduced into the reaction zone as a coordination complex of ruthenium containing halogen ligands or it may be introduced as separate components, the ruthenium compound and the halogen ligand introduced separately. Specific examples of ruthenium compounds suitable for the practice of this invention include iodide-containing ruthenium salts such as ruthenium(III) triiodide, and ruthenium dicarbonyl diiodide. Alternatively, the catalyst may be prepared by adding the ruthenium to the reaction mixture in an oxide form, as in the case of, for example, ruthenium(IV) dioxide hydrate, anhydrous ruthenium(IV) dioxide and ruthenium(VIII) tetraoxide. It may be introduced into the reaction zone also as the salt of a mineral acid, as in the case of ruthenium(III) chloride hydrate, ruthenium(III) bromide, anhydrous ruthenium(III) chloride and ruthenium nitrate, or as the salt of a suitable organic carboxylic acid. Here, examples include ruthenium acetate dimer, ruthenium propionate dimer, ruthenium hexafluoroacetylacetonate, ruthenium trifluoroacetate dimer, ruthenium octanoate dimer, ruthenium naphthenate, ruthenium valerate and ruthenium(III) acetylacetonate. The ruthenium may also be further added to the reaction zone as a carbonyl or hydrocarbonyl derivative. Suitable examples in this case include triruthenium dodecarbonyl, hydrocarbonyls such as $H_2Ru_4(CO)_{13}$ and $H_4Ru_4(CO)_{12}$ and substituted carbonyl species such as ruthenium tricarbonyl trichloride.

The rhodium component may be added to the reaction zone as a coordination complex of rhodium containing halogen ligands or it may be introduced as separate components, the rhodium compound and a halogen compound. As with the ruthenium compounds above, the rhodium compound suitable for adding to the reaction mixture would be dioxides, salts of mineral acids, salts of suitable organic carboxylic acids, or carbonyl or hydrocarbonyl derivatives. Illustrative of rhodium-containing substances which can be conveniently introduced or placed in the reaction zone include, for example, rhodium oxide ($Rh_2O_3$ and $RhO_2$), tetrarhodium dodecacarbonyl, dirhodium octacarbonyl, hexarhodium hexadecacarbonyl ($Rh_6(CO)_{16}$), rhodium formate dimer, rhodium(II) acetate dimer, rhodium(II) propionate dimer, rhodium(II) butyrate dimer, rhodium(II) valerate, rhodium(II) naphthenate, rhodium dicarbonyl acetylacetonate, rhodium tris(acetylacetonate), rhodium trihydroxide, indenylrhodium dicarbonyl, rhodium dicarbonyl (1-phenylbutane-1,3-dione), tris(hexane-2,4-dionato)rhodium(III), tris(heptane-2,4-dionato)rhodium(III), tris(1-phenylbutane-1,3-dionato)rhodium(III), tris(3-methylpentane-2,4-dionato)rhodium(III), tris(1-cyclohexylbutane-1,3-dionato)rhodium(III), rhodium dicarbonyl chloride dimer, rhodium trichloride and hydrate, rhodium hexafluoride, rhodium tribromide, rhodium trinitrate and dihydrate, rhodium sulfate, rhodium sulfite and the like.

As previously noted, while the iodine component of the catalyst system may be combined and added with the ruthenium or rhodium, it is generally preferred to have an excess of iodine present in the catalyst system as a promoting agent. By excess is meant an amount of iodine greater than 3 atoms of iodine per atom of ruthenium+rhodium in the catalyst system. Preferably, the ratio of iodide promoter to rhodium+ruthenium will range from about 4 to about 40, preferably from about 6 to about 20. This promoting component of the catalyst system may consist of iodine, and/or an iodide compound. Suitable iodine compounds include hydrogen iodides, such as hydrogen iodide and aqueous hydriodic acid, alkyl and aryl iodides containing 1 to 12 carbon atoms such as methyl iodide, ethyl iodide, 1-iodopropane, 2-iodobutane, 1-iodobutane, iodobenzene and benzyl iodide as well as acyl iodides such as acetyl iodide. Also suitable as halogen coreactants are the alkali and alkaline earth iodides, ammonium and phosphonium halides. Suitable examples include sodium iodide, cesium iodide, potassium iodide, tetramethylammonium iodide, and tetrabutylphosphonium iodide. Thus, the iodide promoter is selected from iodine, hydrogen iodide, alkyl iodide, aryl iodide, alkali metal iodide, alkaline earth metal iodide, ammonium iodide and phosphonium iodide. A particularly preferred promoter is hydrogen iodide and alkyl ($C_1$–$C_4$) iodide, most preferably hydrogen iodide.

The titanium(IV) component is typically added to the catalyzed system as a titanium(IV) metal compound dissolved in a suitable solvent such as a lower alkanol, or it may be added without solvent to the system utilizing as an in situ solvent the reactant alkanol. The titanium(IV) metal compound used to provide the titanium(IV) component is any suitable titanium compound having titanium in the plus four oxidation state and will readily form a homogeneous solution in the reaction media. Suitable but non-limiting examples of titanium(IV) metal compounds include $TiCl_4$, $TiBr_4$, $Ti(OR)_4$, $Ti(NR_2)_4$ (R is $C_1$–$C_6$) and $TiO(SO_4)$. Preferred titanium(IV) metal compounds are titanium(IV) alkoxides ($C_1$–$C_6$), particularly titanium(IV) isopropoxide. Suitable molar ratios of Ti(IV) to Rh+Ru range from about 1:1 to about 4:1, preferably from about 1.5:1 to about 2.5:1. Titanium(III) metal compounds are not effective promoters.

The quantity of rhodium catalyst employed in the instant invention is not critical and may vary over a wide range. In general, the homologation process is desirably conducted in the presence of a catalytically effective amount of the active ruthenium and rhodium species which give the desired acid products and reasonable yields. Reaction proceeds when employing as little as about $1 \times 10^{-8}$ weight percent, and even lesser amounts of ruthenium+rhodium, basis total weight of the reaction mixture. The upper concentration is dictated by a variety of factors including catalyst costs, partial pressure of carbon monoxide and hydrogen, operating temperature and the utilization of diluent. A ruthenium+rhodium catalyst concentration of from about $1 \times 10^{-5}$ to about 10 weight percent based on the total weight of the reaction mixture is generally desirable. It is further preferable to maintain an excess of ruthenium catalyst species over the rhodium catalyst species. Generally, the molar ratio of ruthenium to rhodium will range from about 1:1 to about 6:1, preferably from about 2:1 to about 4:1.

The temperature range which can be usefully employed in the homologation reaction of the instant process is a variable which is dependent upon other experimental factors including the choice of reactant, pressure, and the concentration and particular choice of catalyst, among other things. The temperature ranges typically from about 150° C. to about 250° C., preferably between about 175° C. and about 225° C.

Pressures utilized in the instant process are superatmospheric pressures. Pressures will range from about 2,000 psi to about 10,000 psi, although higher pressures can be utilized. Preferably, pressures will range from about 2,500 to about 6,000 psi. Optimal pressures will depend on various experimental factors, such as choice of reactants and the particular choice of catalysts utilized.

The feed to the instant process will be an aliphatic alcohol or an aliphatic carboxylic acid or mixtures thereof. These alcohols/acids typically have carbon numbers ranging up to about 20, although higher carbon numbers can be utilized. A hydrogen-to-carbon monoxide ratio of about 1:1 is preferably utilized. Higher amounts of hydrogen tend to increase the hydrocarbon make. A preferred molar ratio of hydrogen-to-carbon monoxide ranges from about 0.5:1 to about 1.2:1.

The invention will be exemplified by the following illustrative embodiments which are provided for illustration only, and are not to be construed as limiting the invention.

ILLUSTRATIVE EMBODIMENTS

In a typical experiment, $RhCl_3$, $RuCl_3$, HI and titanium(IV) isopropoxide are added to 40 ml of methanol in a 100 ml Hastelloy B autoclave. The autoclave is sealed, pressured with 1:1 $H_2$:CO, and then vented slowly. The vessel is then repressured with the syngas to 4,700 psi and heated to 185° C., with additional gas being added to maintain a pressure of about 6,000 psi during the entire reaction. After 3 hours at 185° C., the temperature is raised to 205° C. for an additional 7 hours. The autoclave is cooled and the reaction products are analyzed. Results are shown as Examples 1 and 2 in Table I below. In comparative Example A, the titanium promoter has been deleted. In comparative Example B, titanium(III) chloride has been substituted for the titanium(IV) isopropoxide. In comparative Example C, sodium hydroxide has been substituted for the titanium(IV) isopropoxide. As can be seen from looking at the conversion to $C_3$+oxygenated products, the titanium(III) compound is an ineffective promoter. The use of a base such as sodium hydroxide also provides no promoting effect.

TABLE I

METHANOL HOMOLOGATION

| Example | Catalyst (mmol) | Product Analysis (% w) | | | | | | | | | | |
|---|---|---|---|---|---|---|---|---|---|---|---|---|
| | | A | B | C | D | E | F | G | H | I | J | K |
| 1 | $RhCl_3$ (0.4) $RuCl_3$ (1.1) $Ti(OC_3H_7)_4$ (2.6) HI (25.2) | 0.0 | — | 59.3 | — | 9.1 | 9.8 | 14.6 | — | 4.6 | 2.1 | 0.5 |
| 2 | $RhCl_3$ (0.4) $RuCl_3$ (1.1) $Ti(OC_3H_7)_4$ (5.3) HI (25.2) | 0.0 | — | 74.1 | 0.4 | 7.0 | 2.5 | 13.6 | — | 0.3 | 1.4 | 0.7 |
| A | $RhCl_3$ (0.4) $RuCl_3$ (1.1) HI (25.2) | 0.0 | — | 57.2 | 7.6 | 13.3 | 3.8 | 14.3 | — | 1.6 | 1.5 | 0.7 |
| B | $RhCl_3$ (0.4) $RuCl_3$ (1.1) $TiCl_3$ (1.3) HI (25.2) | 0.0 | 0.4 | 72.3 | 0.7 | 9.3 | — | 15.4 | — | 0.7 | 0.7 | 0.5 |
| C | $RhCl_3$ (0.4) $RuCl_3$ (1.1) NaOH (5.0) HI (25.2) | 0.0 | — | 89.1 | — | — | — | 9.4 | — | — | 0.6 | 0.9 |

A = $CH_3OH$
B = $CH_3CH_2OCH_3$
C = $CH_3CO_2H$
D = $CH_3CH_2OH$
E = $CH_3CO_2CH_2CH_3$
F = $CH_3CH_2CO_2CH_2CH_3$
G = $CH_3CH_2CO_2H$
H = $(CH_3CH_2CH_2)_2O$
I = $CH_3CH_2CO_2CH_2CH_2CH_3$
J = $CH_3CH_2CH_2CO_2H$
K = $CH_4 + C_2H_6$.

I claim:

1. A process for homologating as feed a reactant aliphatic alcohol having a carbon number from 1 to about 20 to a series of homologous aliphatic carboxylic acids having one or more carbon atoms than the reactant alcohol which comprises contacting the reactant alcohol with hydrogen and carbon monoxide at a temperature ranging from about 150° C. to about 250° C. and a pressure ranging from about 2,000 psi to about 10,000 psi in the presence of a homogeneous catalyst comprising a catalytically effective amount of ruthenium and rhodium and an iodide promoter and a titanium(IV) promoter, wherein the molar ratio of ruthenium to rhodium ranges from about 2:1 to about 4:1, the molar ratio of iodide to ruthenium plus rhodium ranges from about 6:1 to about 20:1, and the molar ratio of titanium(IV) promoter to ruthenium plus rhodium ranges from about 1.5:1 to about 2.5:1 and the titanium(IV) promoter is selected from titanium(IV) $C_1$–$C_6$ alkoxides.

2. The process of claim 1 wherein the titanium(IV) promoter is titanium(IV) isopropoxide.

* * * * *